United States Patent
Kitagaki et al.

[11] 3,975,446
[45] Aug. 17, 1976

[54] METHOD FOR THE PREPARATION OF UNSATURATED KETONES

[75] Inventors: Tetsuro Kitagaki, Joetsu; Akira Yamamoto, Niigata; Toshinobu Ishihara, Yono, all of Japan

[73] Assignee: Shinetsu Chemical Company, Tokyo, Japan

[22] Filed: June 25, 1974

[21] Appl. No.: 482,894

[30] Foreign Application Priority Data
June 26, 1973 Japan.................. 48-72094

[52] U.S. Cl................... 260/593 R; 260/586 R; 260/595; 260/488 F; 260/488 J; 260/488 CD
[51] Int. Cl.².................. C07C 45/00; C07C 45/18
[58] Field of Search............. 260/593 R, 586, 595, 260/593, 586 R, 590

[56] References Cited
UNITED STATES PATENTS

| | | | |
|---|---|---|---|
| 2,795,617 | 6/1957 | Kimel et al. | 260/593 |
| 2,839,579 | 6/1958 | Kimel et al. | 260/593 |

OTHER PUBLICATIONS
Marcus et al., J. Org. Chem., 1966, pp. 1369–1372.

*Primary Examiner*—James O. Thomas, Jr.
*Assistant Examiner*—James H. Reamer
*Attorney, Agent, or Firm*—Toren, McGeady and Stanger

[57] ABSTRACT

Unsaturated ketones represented by the general formula

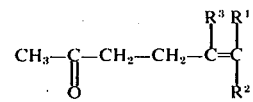

are successfully synthesized with very good yield from corresponding unsaturated alcohols and diketene in a single-step process in which the esterification reaction and the decarboxylation reaction take place concurrently by the synergistic action of the catalyst system composed of a high-boiling amine and an aluminum trialkoxide.

13 Claims, No Drawings

METHOD FOR THE PREPARATION OF UNSATURATED KETONES

FIELD OF THE INVENTION

This invention relates to a novel method for the preparation of unsaturated ketones, or more particularly to a method for the preparation of unsaturated ketones by the reaction of unsaturated alcohols and diketene in a single step process in which the unit reactions of the esterification, carboxylation and rearrangement can be simultaneously involved.

DESCRIPTION OF THE PRIOR ART

In the prior art for the preparation of unsaturated ketones, an unsaturated alcohol (I) is reacted with diketene (II) to produce an ester of acetoacetic acid (III) as shown by the reaction formula (1) below and the acetoacetic acid ester thus produced is then converted to the unsaturated ketone (IV) by decarboxylation and rearrangement (hereinafter this step of the two combined reactions is called simply the decarboxylation reaction) as shown by the reaction formula (2).

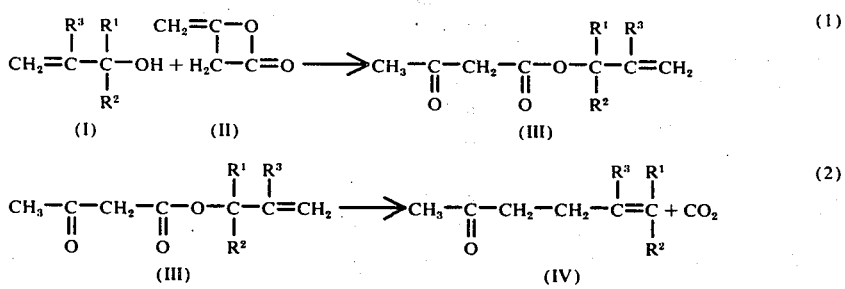

However, the prior art method is disadvantageous as will be explained below. The esterification reaction (1) requires the presence of a catalyst of a basic substance, such as, potassium hydroxide, sodium methoxide, sodium acetate, and pyridine and is carried out at a temperature below 30°C. When the reaction temperature is raised above 30°C for the purpose to accelerating the reaction, the selectivity of reaction (1) is decreased by the predomination of the side reaction by which a high-boiling material is formed which supposedly is a polymer of diketene and the isolation and purification of the acetoacetic acid ester from the reaction mixture become difficult resulting in the very low yield of the acetoacetic acid ester. The yield of the unsaturated ketone by reaction (2) is rather low when the reaction is carried out without the use of catalysts or when the acetoacetic acid ester employed as the starting material of reaction (2) is crude and has not been purified.

On the other hand, U.S. Pat. No. 2,795,617 discloses an improved method wherein the acetoacetic acid ester prepared according to reaction (1) above at 25° to 30°C is, after isolation and purification from the reaction mixture, subjected to the decarboxylation reaction in the presence of an aluminum trialkoxide, having lower alkoxy groups, to give the unsaturated ketone. This method, however, has a disadvantage in that it is a two-step process involving the step of the preparation of the acetoacetic acid ester and the step of the decarboxylation. In addition, the acetoacetic acid ester to be subjected to the decarboxylation reaction must be purified in order to obtain a good yield of the unsaturated ketone, and, further, careful temperature control is an utmost requisite for the smooth performance of the reaction because the decarboxylation reaction is highly exothermic.

The present invention presents an improved novel method for the preparation of the unsaturated ketones wherein the above-mentioned disadvantages of the prior art are avoided.

SUMMARY OF THE INVENTION

According to the present invention, an unsaturated alcohol represented by the general formula

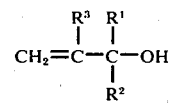

where $R^1$ is a saturated or unsaturated aliphatic or aromatic monovalent hydrocarbon group, $R^2$ is a lower alkyl group and $R^3$ is a hydrogen atom or a lower alkyl group, is subjected to reaction with diketene in the presence of a high-boiling amine, preferably a tertiary amine, an aluminum trialkoxide, having lower alkoxy groups, as the combined catalysts. The method can give a very good yield of the unsaturated ketone and is substantially a single-step process wherein the unsaturated alcohol as the starting material reacts with diketene by the catalytic action of the tertiary amine in the reaction mixture to form the corresponding acetoacetic acid ester, which then is converted to the unsaturated ketone with the evolution of carbon dioxide gas by the catalytic action of the aluminum trialkoxide.

To further explain the invention, diketene is a very reactive compound and is apt to polymerize into a resinous material. It was generally thought impractical to carry out the additional reaction of diketene with another compound at relatively high temperatures in the presence of alkaline substances, because the tendency of diketene to polymerize is significantly enhanced in an alkaline or basic medium as is the case in the method of the present invention, where extremely good results can be obtained in contrast to the results expected from the teachings of the prior art.

The reasons for these unexpected results may be to be presumed as follows. Firstly, the acetoacetic acid ester (III) as the intermediate product is immediately converted to the ketone (IV) by the decarboxylation reaction under the influence of the aluminum catalyst which is co-existent in the reaction mixture, thus rendering the effective concentration of the ester (III) in the reaction mixture substantially negligible. Secondly, the polymerization reaction of diketene, which completes with the ester formation reaction, becomes less predominant due to the relatively weak basicity of the tertiary amine. Thirdly, the synergistic action of the amine and the aluminum trialkoxide has a different catalytic effect from the action in those cases where the amine alone or the aluminum alkoxide alone are employed separately as the single-component catalyst. For example, because of the coordination or very close proximity of the amine molecules to the molecules of the aluminum compound, the reaction of the ester formation and the subsequent decarboxylation reaction take place, microscopically speaking, in one and the same site thus leading to the suppression of the side reactions during the decarboxylation. Lastly, the temperature control in the decarboxylation reaction (2) can be performed in a relatively easy way in which the unsaturated alcohol and diketene as the starting materials are added to the reaction mixture portionwise little by little or the solvent is added to the reaction mixture in which the catalysts have been dissolved in advance. Therefore, the reaction of the ester formation takes place selectively in predominance over the side reactions such as the polymerization of diketene and the yield of the subsequent decarboxylation becomes very high.

As shown above, the unsaturated alcohol as one of the starting material is represented by the general formula

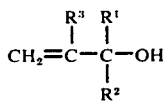

where $R^1$ is a saturated or unsaturated aliphatic or aromatic monovalent hydrocarbon group exemplified by alkyl groups, such as, methyl, ethyl, isobutyl, 4-methylpentyl, 3,4-dimethylpentyl, 4,8-dimethylnonyl and 4,7,8-trimethylnonyl; alkenyl groups, such as, 3-pentenyl, 4-methyl-3-pentenyl, 4-methyl-3-hexenyl, 3,4-dimethyl-3-pentenyl and 4,6-dimethyl-3-heptenyl; alkapolyenyls, such as, 4,8-dimethyl-3,7-nonadienyl; cyclic alkyl or cyclic alkenyl groups, such as, cyclohexyl, cyclohexenyl and cyclohexylmethyl; and aryl groups, such as, phenyl and tolyl, $R^2$ is a lower alkyl group, such as methyl, ethyl and isobutyl and $R^3$ is a hydrogen atom or a lower alkyl group, such as, methyl, ethyl and isobutyl. Several of the examples of those unsaturated alcohols are 2,3-dimethyl-1-buten-3-ol, 3-methyl-1-buten-3-ol, 3,7-dimethyl-1,6-octadien-3-ol, 3,7,11-trimethyl-1-dodecen-3-ol, 3,7-dimethyl-1-octen-3-ol, 3,6,7-trimethyl-1,6-octadien-3-ol, 3,7,11-trimethyl-1,6,10-dodecatrien-3-ol and 3-phenyl-1-buten-3-ol. The counterpart of the starting reactants, diketene, may be of ordinary commercial grade.

The amines employed as the catalyst in the method of the present invention are limited to those having a relatively high boiling point, for example, higher than 130°C and are, exemplified by quinoline, dimethylaniline, dimethylpyridine and ethylpyridine. The reason for such a limitation is that amines having lower boiling points, if employed instead of the high-boiling amines, will be by being carried away by the carbon dioxide gas evolved in the course of the decarboxylation reaction in the reaction mixture. In addition, the reaction temperature is limited to a lower value by virtue of refluxing of the low-boiling amines resulting in the retardation of the reaction. Incidentally, alkaline catalysts with stronger basicity than the high-boiling amines, such as potassium hydroxide, sodium methoxide and sodium acetate, do not give satisfactorily high yields of the desired unsaturated ketone because their basicities are too high and their dispersibilities in the reaction mixture are poor.

The other component of the catalyst system employed in combination with the above-described high-boiling amine in the present invention is an aluminum trialkoxide, having lower alkoxy groups exemplified by ethoxy, isopropoxy, n-butoxy and tertiary butoxy groups. It is preferable to employ aluminum triisopropoxide as the trialkoxide. The use of the aluminum trialkoxide is indispensable in the method of the present invention because the omission of the aluminum trialkoxide makes it necessary to carry out the decarboxylation reaction at much higher temperatures, for example at from 170° to 190°C, leading inevitably to the predominance of the side reactions, such as, the polymerization of diketene and decomposition or polymerization of the unsaturated alcohol and the acetoacetic acid ester, which means a great decrease in the yield of the unsaturated ketone.

It is a recommended procedure in the performance of the method of the present invention that the heat evolution in the initial stage of the reaction be mitigated and the smooth progress of the reaction be attained by first dissolving or dispersing the high-boiling amine and the aluminum trialkoxide in a suitable diluent solvent to form a solution or a dispersion and subsequently dropping it into the unsaturated alcohol and diketene as the starting reactants, either separately or together in a mixture. The reaction temperature is preferably within the range of from 135° to 170°C to obtain the unsaturated ketone with a satisfactory yield and, when the reaction temperature is too low, the velocity of the reaction becomes impractically low while too high reaction temperatures result in increased amounts of the byproducts with higher or lower boiling points due to the polymerization of diketene and the decomposition and polymerization of the intermediate acetoacetic acid ester.

The molar ratio of the two reactants, namely the unsaturated alcohol and diketene, must be determined with a deliberate consideration. For example, from 1.0 to 2.0 moles, preferably from 1.05 to 1.20 moles, of diketene should be employed per mole of the unsaturated alcohol from the sole standpoint of obtaining the highest yield of the unsaturated ketone. However, it is economically disadvantageous to employ diketene in excess over the equimolar amount to the unsaturated alcohol because of the expensive and futile consumption of diketene by the polymerization of the excess portion of it. Therefore, it is usually advantageous to employ less than equimolar amount of diketene to the unsaturated alcohol.

The high-boiling amine as the catalysts is added to the reaction mixture in an amount of from 0.002 to 0.04 moles per mole of the unsaturated alcohol and the aluminum trialkoxide is employed in an amount of more than 0.002 moles, preferably from 0.01 to 0.03 moles, per mole of the unsaturated alcohol.

The selection of the diluent solvent utilized in the method of the present invention as the reaction medium is not critical so long as the aluminum trialkoxide is able to be dissolved or uniformly dispersed in it, although it is preferably an inert solvent with a boiling point higher than 150°C because the reaction is carried out at a temperature between 135° and 170°C as mentioned above. It is exemplified by tetralin diphenylether, or the unsaturated ketone, which is the product of the method itself, may be successfully employed as the inert solvent of the reaction medium.

Examples of the present invention are given below to illustrate the method together with the controls.

EXAMPLE 1

Into a 1-liter volume, three-necked flask equipped with a stirrer, a thermometer, a dropping funnel and a reflux condenser and connected to a gas flow meter were put 3 g each of the high-boiling amines shown in Table 1 and each of the aluminum trialkoxides shown in the table in the amount as indicated, and they were dispersed in 10 g of 5,6-dimethyl-5-hepten-2-one. The reaction mixture was heated to the reaction temperature shown in the table. To the resulting reaction mixture was added dropwise a mixture of 200 g (2.0 moles) of 2,3-dimethyl-1-buten-3-ol and the indicated amount of diketene over the period of 2 hours. The evolution of carbon dioxide gas began immediately after the start of the dropping of the reactants. Stirring was continued for about 20 minutes at the same temperature after the completion of the dropping of the reactants, and the reaction mixture was then cooled and subjected to distillation under reduced pressure to give 5,6-dimethyl-5-hepten-2-one with the boiling point of 67 to 68°C/8 mmHg and the refractive index of 1.4518 at 20°C with the yields based on the amounts of 2,3-dimehtyl-1-buten-3-ol taken as shown in the table.

The purity of 5,6-dimethyl-5-hepten-2-one obtained above was assayed by means of gas chromatography and found to be from 99.0 to 99.6%.

Experiment 3 in the table was conducted in such a manner that the unreacted 2,3-dimethyl-1-buten-3-ol was continuously extracted out of the reaction system little by little through the rectification column interposed between the flask and the reflux condenser.

In Experiment 5, some difficulties were encountered in the temperature control and pyridine was lost in the course of the reaction giving rise to a retardation of the reaction which necessitated the addition of 2 g of pyridine.

The results of Experiments 6 and 7 as controls were unsatisfactory by the very low reaction velocity in the former and by the formation of large amounts of the byproducts with higher or lower boiling points in the latter.

and 6 g of aluminum triisopropoxide and the latter two were dispersed in the former. The temperature was raised to 150°C. Then, a mixture of 172 g (2.0 moles) of 3-methyl-1-buten-3-ol and 185 g (2.2 moles) of diketene was dropped over the period of 2 hours while the temperature was kept at 152±3°C. The evolution of carbon dioxide gas began to take place immediately after the start of the dropping. The reaction mixture was cooled when the evolution of carbon dioxde gas had almost ceased after about 10 minutes from the completion of the dropping and then subjected to distillation under reduced pressure to give 213 g of 6-methyl-5-hepten-2-one with the boiling point of 58.0 to 59.0°C/9 mmHg and the refractive index of 1.4402 at 20°C in 89.5% yield based on the amount of 3-methyl-1-buten-3-ol taken as the starting material.

EXAMPLE 3

The procedure was the same as in the preceding example except that the diluent solvent was 10 g of 6,10-dimethyl-5,9-undecadien-2-one and the unsaturated alcohol as the starting material was 308 g (2.0 moles) of 3,7-dimethyl-1,6-octadien-3-ol. 6,10-Dimethyl-5,9-undecadien-2-one with the boiling point of 120° to 121°C/10 mmHg and the refractive index of 1.4664 at 20°C was obtained in an amount of 320 g corresponding to 87.5% yield based on the amount of 3,7-dimethyl-1,6-octadien-3-ol.

EXAMPLE 4

The procedure was the same as in Example 2 except that the diluent solvent was 10 g of tetraline and the starting reactants were 226 g (1.0 mole) of 3,7,11-trimethyl-1-dodecen-3-ol and 101 g (1.2 moles) of diketene. 6,10,14-Trimethyl-5-pentadecen-2-one with the boiling point of 123° to 125°C/1 mmHg and the refractive index of 1.4560 at 20°C was obtained in an amount of 212 g corresponding to 84.7% yield based on 3,7,11-trimethyl-1-dodecen-3-ol.

EXAMPLE 5

The procedure was the same as in Example 2 except that the diluent solvent was 10 g of 6-phenyl-5-hepten-2-one and the unsaturated alcohol was 196 g (2.0 moles) of 3-phenyl-1-buten-3-ol. 6-Phenyl-5-hepten-2-one with the boiling point of 113° to 115°C/1 mmHg and the refractive index of 1.5400 at 20°C was obtained in an amount of 265 g corresponding to 80.5% yield based on 3-phenyl-1-buten-3-ol.

What is claimed is:

1. A method for the preparation of an unsaturated ketone represented by the general formula Table 1

| Experiment No. | Present Invention | | | | | Control | |
|---|---|---|---|---|---|---|---|
| | 1 | 2 | 3 | 4 | 5 | 6 | 7 |
| Diketene, amount, g | 185 | 240 | 168 | 185 | 185 | 185 | 185 |
| (moles) | (2.14) | (2.85) | (2.00) | (2.14) | (2.14) | (2.14) | (2.14) |
| High boiling Amine | Quinoline | γ-Ethyl pyridine | Quinoline | Dimethyl aniline | Pyridine | Quinoline | Quinoline |
| Aluminum Alkoxy Trialkoxide Amount, g | Isopropoxy 4 | Isopropoxy 7 | Isopropoxy 4 | Ethoxy 4 | Isopropoxy 4 | Isopropoxy 0.4 | None — |
| Reaction Temp. °C | 152±3 | 160±5 | 152±3 | 152±3 | 152±10 | 152±3 | 175±5 |
| Yield, % | 90.5 | 91.0 | 79.4 | 84.5 | 68.5 | 18.3 | 42.5 |

EXAMPLE 2

Into a flask identical to one used in Example 1 were put 10 g of 6-methyl-5-hepten-2-one, 3 g of quinoline

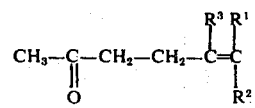

where $R^1$ is a saturated or ethylenically unsaturated aliphatic cycloaliphatic or aromatic monovalent hydrocarbon group, $R^2$ is an alkyl group having from 1 to 6 carbon atoms, and $R^3$ is a hydrogen atom or an alkyl group having from 1 to 6 carbon atoms, which comprises subjecting an unsaturated alcohol represented by the general formula

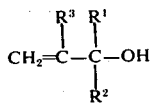

where $R^1$, $R^2$ and $R^3$ are as defined above, to a reaction with diketene at a temperature in the range from 135° to 170°C in the presence of a tertiary amine having the boiling point higher than 130°C and selected from the group consisting of quinoline, dimethylaniline, dimethylpyridine and ethylpyridine and an aluminum trialkoxide in which the alkoxy groups are lower alkoxy groups having from 1 to 4 of carbon atoms.

2. The method for the preparation of an unsaturated ketone as claimed in claim 1, wherein said reaction is carried out in the presence of a diluent solvent.

3. The method for the preparation of an unsaturated ketone as claimed in claim 2, wherein said diluent solvent is an organic solvent having the boiling point higher than 150°C.

4. The method for the preparation of an unsaturated ketone as claimed in claim 2, wherein said diluent solvent is the same unsaturated ketone as the unsaturated ketone to be produced by said reaction.

5. The method for the preparaion of an unsaturated ketone as claimed in claim 1, wherein $R^1$ is selected from the class consisting of alkyl groups, cycloalkyl groups, alkenyl groups, cycloalkenyl groups and aryl groups.

6. The method for the preparation of an unsaturated ketone as claimed in claim 1, wherein said $R^2$ is selected from the class consisting of methyl, ethyl, propyl, butyl, pentyl and hexyl groups.

7. The method for the preparation of an unsaturated ketone as claimed in claim 1, wherein said $R^3$ is selected from the class consisting of hydrogen atom and methyl, ethyl, propyl, butyl, pentyl and hexyl groups.

8. The method for the preparation of an unsaturated ketone as claimed in claim 1, wherein said tertiary amine is employed in an amount of from 0.002 moles to 0.04 moles per mole of said unsaturated alcohol.

9. The method for the preparation of an unsaturated ketone as claimed in claim 1, wherein said aluminum trialkoxide is employed in an amount of from 0.01 mole to 0.03 mole per mole of said unsaturated alcohol.

10. The method for the preparation of an unsaturated ketone as claimed in claim 1, wherein said $R^1$ and $R^2$ are both methyl groups and said $R^3$ is either a methyl group or a hydrogen atom.

11. The method for the preparation of an unsaturated ketone as claimed in claim 1, wherein said unsaturated ketone is 6,10-dimethyl-5,9-undecadient-2-one and said unsaturated alcohol is 3,7-dimethyl-1,6-octadien-3-ol.

12. The method for the preparation of an unsaturated ketone as claimed in claim 1, wherein said unsaturated ketone is 6,10,14-trimethyl-5-pentadecen-2-one and said unsaturated alcohol is 3,7,11-trimethyl-1-dodecen-3-ol.

13. The method of claim 1 wherein $R^1$ is selected from the group consisting of methyl, ethyl, isobutyl, 4-methyl-pentyl, 3,4-dimethylpentyl, 4,8-dimethylnonyl, 4,7,8-trimethylnonyl, 3-pentenyl, 4-methyl-3-pentenyl, 4-methyl-3-hexenyl, 3,4-dimethyl-3-pentenyl, 4,6-dimethyl-3-heptenyl, 4,8-dimethyl-3,7-nonadienyl, cyclohexyl, cyclohexenyl, cyclohexylmethyl, phenyl, and tolyl.

* * * * *